US006590209B1

(12) United States Patent
Bajt

(10) Patent No.: US 6,590,209 B1
(45) Date of Patent: Jul. 8, 2003

(54) TECHNIQUE TO QUANTITATIVELY MEASURE MAGNETIC PROPERTIES OF THIN STRUCTURES AT <10 NM SPATIAL RESOLUTION

(75) Inventor: Sasa Bajt, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/516,878

(22) Filed: Mar. 1, 2000

Related U.S. Application Data
(60) Provisional application No. 60/122,713, filed on Mar. 3, 1999.

(51) Int. Cl.[7] .............................................. G01N 23/04
(52) U.S. Cl. ...................................... 250/307; 250/311
(58) Field of Search .................................. 250/307, 311

(56) References Cited

U.S. PATENT DOCUMENTS

| | | | | |
|---|---|---|---|---|
| 5,134,288 A | * | 7/1992 | Van Dijck | 250/307 |
| 5,153,434 A | * | 10/1992 | Yajima et al. | 250/311 |
| 5,654,547 A | * | 8/1997 | Coene et al. | 250/307 |

OTHER PUBLICATIONS

Paganin et al., "Noninterferometric Phase Imaging with Partially Coherent Light", Physical Review Letters, vol. 80, No. 12, Mar. 23, 1998, pp. 2586–2589.*

Han et al., "Practical Image Restoration of Thick Biological Specimens Using Multiple Focus Levels in Transmission Electron Microscopy", Journal of Structural Biology, 120 (1997), pp. 237–244.*

Bajt et al., "Quantitative phase–sensitive imaging in a transmission electron microscope", Ultramicroscopy 83 (2000), pp. 67–73.*

D. Van Dyck et al, "A New Procedure For Wave Function Restoration In High Resolution Electron Microscopy", Optik 77, No. 3 (1987) 125–128.

Coene et al., "Phase Retrieval Through Focu Variation For Ultra–Resolution In Field–Emission Ransmission Electron Microscopy", Physical Review Letters, V. 69, No. 26, Dec. 28, 1992.

Kirkland, "Improved High Resolution Image Processing Of Bright Field Electron Micrographs", Ultramicroscopy 15 (1984) 151–172.

* cited by examiner

*Primary Examiner*—Jack Berman
(74) *Attorney, Agent, or Firm*—John P. Wooldridge; Alan H. Thompson

(57) ABSTRACT

A highly sensitive and high resolution magnetic microscope images magnetic properties quantitatively. Imaging is done with a modified transmission electron microscope that allows imaging of the sample in a zero magnetic field. Two images from closely spaced planes, one in focus and one slightly out of focus, are sufficient to calculate the absolute values of the phase change imparted to the electrons, and hence obtain the magnetization vector field distribution.

1 Claim, 3 Drawing Sheets

Phase image (greyscale)

(Surface plot)

(Real Foucault)

(Simulated Foucault)

TECHNIQUE TO QUANTITATIVELY MEASURE MAGNETIC PROPERTIES OF THIN STRUCTURES AT <10 NM SPATIAL RESOLUTION

This invention claims priority to U.S. Provisional Patent Application Serial No. 60/122,713, filed Mar. 3, 1999.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to transmission electron microscopy and more specifically, it relates to the use of a modified transmission electron microscope to image magnetic properties quantitatively.

2. Description of Related Art

Various modes of Lorentz transmission electron microscopy provide high resolution (5–100 nm) together with high sensitivity to the local variation of magnetic induction. The image contrast is a result of the deflection experienced by the electron beam when it interacts with the magnetic induction of the specimen. The most commonly used modes are Foucault and Fresnel imaging. In the Foucault mode an opaque aperture in the back-focal plane selectively stops the electrons deflected in certain orientation corresponding to particular oriented magnetic domains. Those areas appear dark in the image. In the Fresnel mode the domain walls are revealed as narrow light and dark areas when the specimen is out of focus. Both methods are rather easy to implement and are suitable to select a region of interest to be studied by the new quantitative phase-contrast imaging technique described here.

However, the images obtained with the above mentioned methods are only qualitative. Differential phase contrast imaging and a known method of coherent Foucault imaging provide a more quantitative description of the induction variation but they require a highly coherent source. But none of these methods gives absolute values of the magnetic induction.

The only other method to the one that we are describing in this document, that can give the absolute value of the phase and therefore the magnetic induction or magnetization, is the electron holography method. However, this method also requires a highly coherent source (which is extremely expensive), it is technically complicated to do and the reconstruction of the electron holograms requires lots of time and effort.

SUMMARY OF THE INVENTION

It is an object of the present invention to provide a method for measuring magnetic properties quantitatively.

The magnetic microscopy method of the present invention can be used to improve the theoretical models that calculate the magnetic response from first principles by comparing the theoretical calculations and the experimental results to obtain quantitative images.

Quantitative imaging is of interest to the magnetic recording and storage industry to study the magnetic properties of very small structures and correlate them with their crystalline microstructure. The present microscope would enable that industry to understand what is happening on a nanometer scale and to develop better magnetic storage media and magnetic sensors.

The present invention uses a non-interferometric phase contrast imaging technique and applies it to image magnetic domains using electrons. The non-interferometric phase contrast imaging technique using a transmission electron microscope and imaging thin magnetic structures gives absolute phase information but it is desirable to extract the magnetization vector distribution in a magnetic structure. To obtain the magnetization vector distribution, one needs first to calculate the gradient of the phase. The gradient of the phase is proportional to the magnetic induction (B). So, once you have the gradient of the phase, the Lorentz force may be obtained and finally the magnetization vector. The Lorentz force is connected with the magnetic induction (B) by the equation:

$$F=e(v \times B),$$

where e represents the electric charge of the electron, v is the velocity vector of the electron and B is the magnetic induction vector in the material. The magnetization vector can be derived from the following formula:

$$M=(B-H_0)/4 \pi.$$

If the external applied magnetic field ($H_0$) is zero then the magnetization vector is directly proportional to the magnetic induction, otherwise the external magnetic field has to be subtracted.

A description of how to obtain the absolute phase using non-interferometric phase contrast imaging follows. To obtain information about the phase using non-interferometric measurement, one needs to consider that if the electron beam is monochromatic and paraxial, the wave equation can be written in a form called the transport-of-intensity equation. This relates three quantities: the intensity in the plane, the intensity derivative normal to the plane and the phase in the plane. Both the intensity and the intensity derivative can be measured directly. The phase can be calculated from the transport-of-intensity equation as described in Paganin and Nugent's paper (Paganin D., Nugent K. A., 1998, *Phys. Rev. Lett.* 80, 2586) incorporated herein by reference. The algorithm is deterministic and yields a unique solution, provided that there are no dislocations in the phase front. Two intensity measurements in closely spaced planes are needed to determine the phase front. The measurement in focus gives the intensity and the difference between the intensities in focus and out of focus gives the intensity derivative. The intensity derivative contains the information about the phase of the wave in the plane. If, for example, the phase front of the wave has locally some curvature then the electrons will get slightly focused or defocused as they travel from one plane to the other. Therefore the intensity derivative is a measure of the wavefront curvature. The wavefront curvature is a function of both the intensity and the phase of the wave and is proportional to the intensity derivative, as shown in the Paganin and Nugent's paper, as cited above The transport-of-intensity equation gives the intensity derivative as a function of the intensity and the phase. The solution gives the phase as a function of the intensity and the intensity derivative.

The gradient of the phase is proportional to the magnetic induction. The magnetic induction is a sum of the magnetization and the external magnetic field. All the above quantities are vectors, so in additioning to obtain their absolute values, the direction is also extracted. Vector maps, showing the direction and the magnitude of magnetization can be produced. FIG. 1 shows the recovered phase image of cobalt grain. The figure is a greyscale image of the phase structure, which is also represented as a surface plot in FIG. 1B. FIG. 1C shows magnetism extracted from the phase image of FIG. 1A.

To do the experiment one needs a TEM microscope. It is important that this method does not require a highly coherent source because this means it can be easily applied to an older TEM microscope. It is beneficial to set the TEM microscope up to perform the imaging in almost zero magnetic field so that the original magnetic microstructure remains unchanged during the experiment.

In addition it is also possible to observe the dynamic effects by applying a controlled external magnetic field on the specimen or to study the thermal effects by heating the specimen in-situ. The images are recorded digitally with CCD camera with large dynamic range. The usual data file consists of (1024×1024)×16 bits. Specimens have been deposited directly on a thin silicon nitride membrane to avoid any extra sample preparation. The samples imaged were cobalt structures ranging from 10 to 50 nm in thickness. The monochromatic electrons used in the experiments had an energy of 200 keV (wavelength=$2.5 \times 10^{-12}$ m) although some experiments were performed using electrons with lower energies. The use of higher energy electrons is preferable because they give a higher spatial resolution. Using 200 keV electrons and the modification described above improved the spatial resolution to about 10 nm. The TEM samples have to be transparent to the electron beam to get an image of the specimen, but the maximum thickness allowed is a strong function of the density of the specimen and of the energy of the electrons. Co structures were able to be imaged that were 100 nm thick and deposited on 40 nm silicon nitride membranes. In order to do the calculations two to three images taken under the same experimental conditions of the same specimen are needed. The images have to be taken as close in time to each other as possible to minimize the drift in the image. A computer code may be used to correct for such drift. Usually an image in focus, one over-focused and one under-focused are taken. Steps of 0.23·m seem to give good results for the 200 keV electrons. In addition to the digital images the parameters needed to perform the calculation are the wavelength of the electrons, the thickness of the structure, the image size and the defocus value. It usually takes only few seconds to record one image and few seconds of computer time to do the calculations to obtain the quantitative phase contrast images.

The above mentioned TEM modification does not interfere with the conventional TEM mode. Actually, the specimen is usually placed high above the objective to do quantitative phase contrast imaging and then just above the objective lens to do the conventional microscopy, such as to study the micro-crystallinity, the micro-diffraction and micro-composition. The spatial resolution when imaging magnetic domains is around 10 nm. This spatial resolution is limited only by the spatial resolution of the TEM under those conditions. This means that much higher spatial resolution could be achieved on a newer TEM microscope.

When a wavefield is incident on a sample both its intensity and its phase are modified. For many samples of interest in the electron microscopy of biological samples and of materials, the modulation of the intensity of the wave can be negligibly small, whereas the impact on the phase may be quite strong. There is therefore a great deal of interest in the imaging of phase in electron microscopy.

A number of techniques have been evolved that allow the phase to be rendered visible, including Zernike phase contrast and Foucault imaging. However, neither of these techniques allows the phase to be determined quantitatively. For the phase to be measured, electron holography may be used. This technique requires a highly coherent electron source and so is not possible using a conventional transmission electron microscope.

DETAILED DESCRIPTION OF THE INVENTION

Figure 1A:
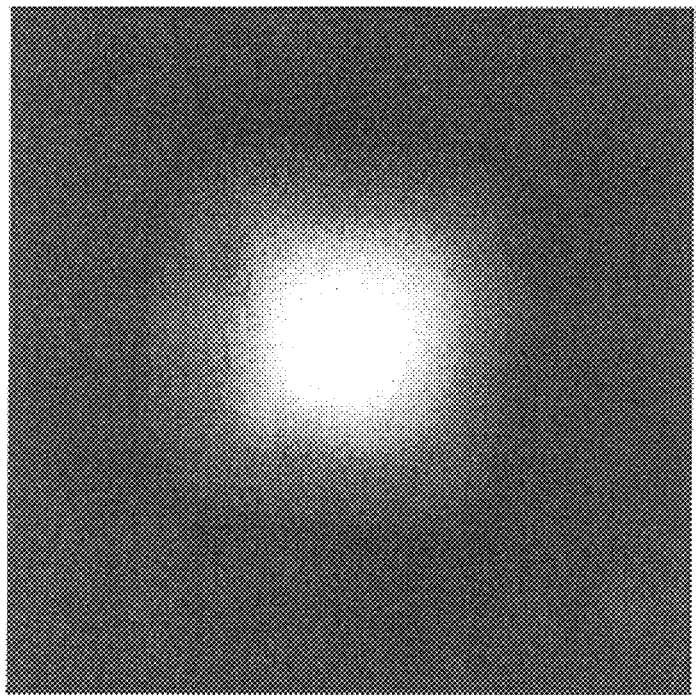
FIG. 1A shows a recovered phase image of cobalt grain.

The invention determines the phase and amplitude of a high voltage electron wave passing through a sample using a conventional high voltage transmission electron microscope. One important application of phase-sensitive TEM is to the study of magnetic materials for the development of magnetic storage devices. The present method characterizes a magnetic sample using established electron holography techniques and compares the results with a non-interferometric approach. Apart from a consistent calibration factor, the phase images are in quantitative agreement.

Consider a sample illuminated by an electron wave. For purposes of this discussion, ignore the imaging properties of the microscope. The time-averages probability current of an electron wave, $<\vec{j} \diamond \vec{r} \bigcirc>$, obeys the continuity equation $\Box \cdot <\vec{j}(\vec{r})>=0$. Assuming that there are no topological phases present, this current may be written in the form $$<\vec{j}(\vec{r})>=1/m_e \rho(\vec{r}) \Box \phi_s(\vec{r}) \qquad (1)$$

where $\rho(\vec{r})$ is the probability density and $\phi_s(\vec{r})$ is the so-called scalar phase of the wavefield. The scalar phase reduces to the conventional phase in the case of a coherent wave, such as is used in electron holography. However, the present method does not assume a coherent wave. Furthermore, a knowledge of $\rho(\vec{r})$ associated with the continuity equation, serves to define the phase $\phi_s(\vec{r})$ uniquely.

If this partially coherent wavefield passes through a two-dimensional sample, the probability current leaving the sample has the form $$<J_{out}(\vec{r})>=\rho(\vec{r})T_{obj}(\vec{r})\Box\{\phi_s(\vec{r})+\phi_{obj}(\vec{r})\} \qquad (2)$$

Where $T_{obj}(\vec{r})$ is the intensity (probability) transmission of the object and $\phi_{obj}(\vec{r})$ is the phase shift induced by the object.

An image of the outgoing wave field is then obtained, which is assumed to be perfect, and then a measurement is taken of the longitudinal probability gradient. If it is assumed that both $\rho(\vec{r})$=constant, and $\phi_s(\vec{r})$=constant in the incident wave, then $$\frac{\partial \rho(\vec{r})}{\partial z} = \frac{\hbar}{p} \nabla \cdot (T_{obj}(\vec{r}) \nabla \phi_{obj}(\vec{r})) \quad (3)$$

An equation of this form, the Nugent et al. transport-of-intensity equation, may be readily solved for the phase given a measurement of $T_{obj}(\vec{r})$.

In the experiments reported here, then, an electron image is formed of a sample and then the image is differentially defocused on either side of best focus to form a measurement of $$\frac{\partial \rho(\vec{r})}{\partial z}.$$

Eq(3) is then solved using this data to determine the phase quantitatively and independently of the amplitude.

As a test object, 2×2 μm cobalt squares were imaged using a conventional TEM (JEOL 200CX STEM). The magnetic microstructures consisted of the Co squares fabricated directly on 40 nm thick, silicon nitride membranes supported by silicon frames.

The electromagnetic lenses in the TEM are surrounded by strong magnetic fields that can alter or completely destroy the magnetic information in the specimen, thus it is important that the specimen sits in a magnetic field-free region. This was achieved using appropriately designed low-field lenses. A a second side entry goniometer was installed to the TEM column above the objective lens. With the objective lens energized, less than 0.5 Gauss was measured in the new specimen position. The image was acquired using a 1024× 1024 pixel Gatan CCD camera and the microscope was operated at 200 keV with a magnification of 5650×.

The nominal minimum focus step size possible at this magnification was 0.23 μm, so images were collected in 5 planes spaced 0.23 μm apart either side of best focus in addition to the plane of best focus. Because the images drifted slightly between exposures, the raw intensity images were aligned to each other using an autocorrelation routine prior to processing. In this way, five measurements of the object phase structure were obtained. Failure to properly align the images results in the addition of a spurious tilt artifact to the recovered phase images. Although this phase tilt can be subsequently removed, it is preferable to correctly align the raw data. All five of these independently processed data sets are indistinguishable apart from slight variations in the magnitude of the recovered phase, a variation which is attributable to slight variations in the de-focus distance.

Figure 1B:
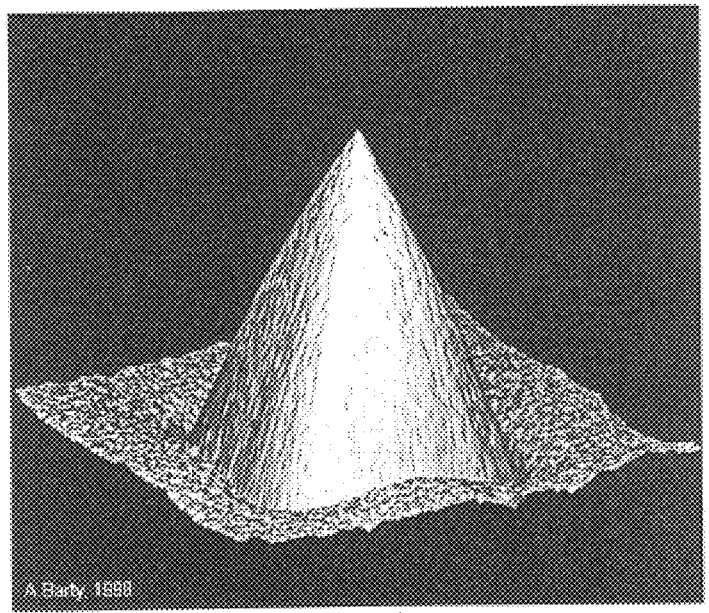
FIG. 1B shows a surface plot of the phase structure of FIG. 1A.

The recovered phase for the pair of images at a de-focus distance of ±3×0.23 μm is shown as a surface plot in FIG. 1A. This image is produced directly by processing the data using equation (3). Note that is not necessary to unwrap this phase even though it has gone through many cycles of 2π. Note also that the phase map has a dimpled appearance, as shown in FIG. 1B. These features are due to slight thickness variations in the silicon nitride substrate, as can be seen by the fact that these pits extend outside the cobalt dot itself onto the surrounding substrate.

Figure 1C:
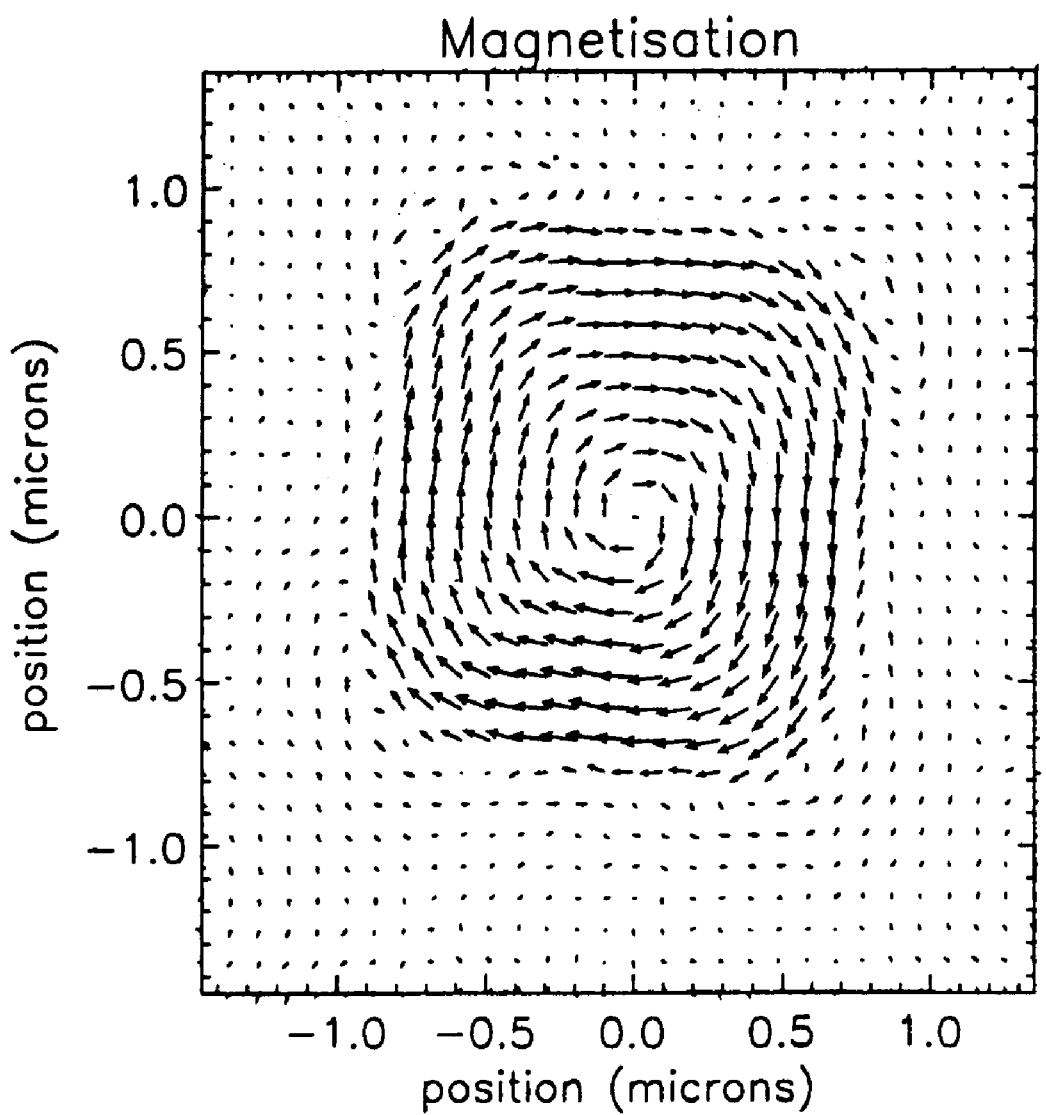
FIG. 1C shows magnetism extracted from the phase image of FIG. 1A.

The electrons are deflected perpendicular to the direction of magnetization by an amount proportional to the magnitude of the magnetization enabling computation of the sample magnetization directly from the phase image and production of a magnetization image as shown in FIG. 1C. As can be seen, the cobalt square consists of a single magnetic domain and displays the classic vortex pattern expected of such a structure.

Figure 2A:
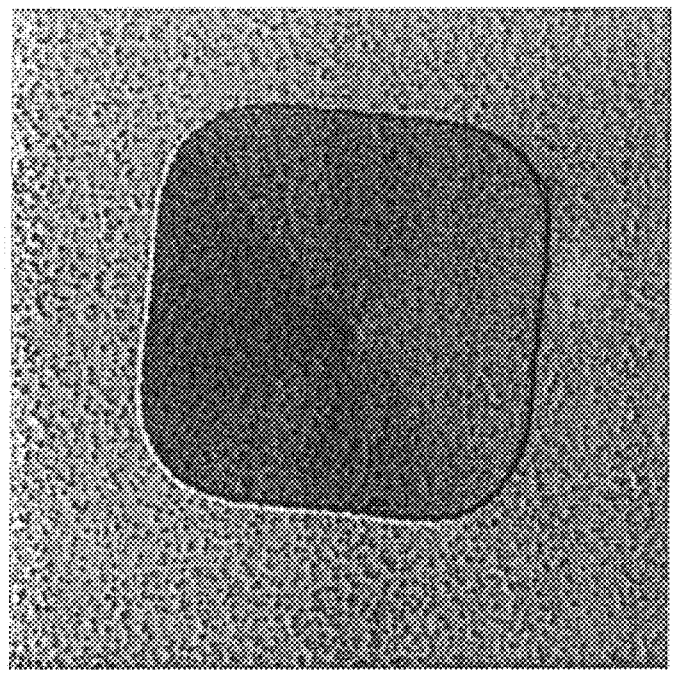
FIG. 2A shows a recovered Foucault image of a square under examination.
Figure 2B:
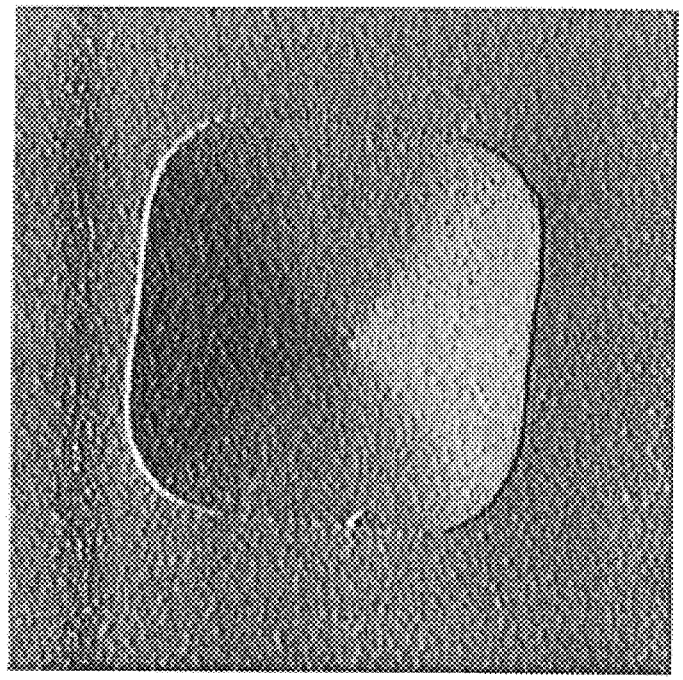
FIG. 2B shows a Foucault image calculated using the phase data.

The direct image of the square yields the probability distribution transmitted by the sample, and therefore also probability amplitude. This information, when combined with the phase map, permits a full characterization of the wavefield leaving the sample. It is therefore possible to use this information to calculate the image that would be produced by any other imaging technique. This observation allows an independent test of the accuracy of the phase information. The phase structure using the Foucault imaging technique renders the phase gradient in a particular direction visible as an intensity variation. A Foucault image of the square under examination was obtained and the Foucault image was calculated using the phase data. The two images are shown in FIGS. 2A and B. Except for some differences in contrast, the two images are virtually identical.

An important aspect of this work, however, is the demonstration that the phase we have obtained is quantitatively correct. To confirm this, off-axis electron holographic images of the Co square were obtained. The relatively large size of the squares used in this demonstration required take four holograms per square were taken. For each of these holograms, half the field of view was covered with the sample and the other half with the surrounding silicon nitride membrane. A biprism wire carrying a voltage of 120V was employed to cause overlap between the electron wave that has passed through the sample on the top of the silicon nitride membrane and a reference wave that has passed only through the silicon nitride membrane. The thickness of the silicon nitride membranes is quite uniform, allowing the assumption that the effect of the silicon nitride thickness is the same for both waves. The contribution of the membrane to the absolute phase of the sample is therefore only an additional constant that is not observable with the present technique.

The profiles obtained using the present method and the holography method were compared. With a predetermined calibration factor, the phase gradient measured using the direct imaging technique described here was 0.0246±0.0010 nm/rad, and that measured using electron holography was found to be 0.0246±0.0003 nm/rad. Clearly the agreement is excellent. Thus the two measurement may be reconciled by an appropriate calibration of the TEM being used. Thus, once the TEM has been calibrated, a quantitatively accurate measurement of the electron phase may be obtained.

Thus, in summary, the present invention is a new method for high-resolution electron phase imaging. Its accuracy has been demonstrated through the direct observation of the magnetization in magnetic microstructures. The results obtained are identical in form to independent measurements. The magnitude of the phase shift differs from independent holographic measurements by a sample independent calibration factor that is removed through an appropriate calibration of the TEM.

Although this technique has been demonstrated using magnetic samples, the technique described here can be used to image any sample, magnetic or otherwise, which introduces a phase shift into an electron beam. Note also that, because the present technique solves for only the phase component of the transmitted electron wave, the phase and intensity structure of the sample may be clearly separated. The technique described here provides a powerful and simple imaging modality that offers new ways of seeing samples in all areas where TEM has a role to play.

Changes and modifications in the specifically described embodiments can be carried out without departing from the scope of the invention, which is intended to be limited by the scope of the appended claims.

What is claimed is:

1. A method for quantitatively measuring the magnetization vector field of a magnetic structure, comprising:

illuminating a magnetic structure with an electron wave;

forming an electron image of said magnetic structure with said electron wave, wherein said electron image comprises pixels;

measuring the intensity of said electron image;

forming a defocused image of said electron image on either side of best focus;

measuring the intensity of said defocused image;

determining the difference between the intensity of said electron image and said defocused image to obtain the phase gradient;

using the Nugent et al. transport-of-intensity equation, determining the phase of said magnetic structure quantitatively from said phase gradient;

calculating the phase difference in the x-direction to obtain the magnetization vector in the x-direction; and calculating the phase difference in the y-direction to obtain the magnetization vector in the y-direction.

* * * * *